United States Patent [19]

Larock

[11] Patent Number: 4,563,537

[45] Date of Patent: Jan. 7, 1986

[54] SYNTHESIS OF THIOPHENE-CONTAINING PROSTAGLANDIN ENDOPEROXIDE APPARATUS

[75] Inventor: Richard C. Larock, Ames, Iowa

[73] Assignee: Iowa State University Research Foundation, Inc., Ames, Iowa

[21] Appl. No.: 617,224

[22] Filed: Jun. 4, 1984

Related U.S. Application Data

[62] Division of Ser. No. 423,789, Sep. 27, 1982, Pat. No. 4,520,207.

[51] Int. Cl.$^4$ .................... C07D 333/24; A61K 31/38
[52] U.S. Cl. ........................................ 549/79; 549/22; 549/32; 549/60; 549/76; 549/77; 549/78; 544/235; 546/141; 546/153; 514/444; 514/438
[58] Field of Search ....................... 549/79, 22, 32, 60, 549/76, 77, 78; 544/235; 546/141, 153

[56] References Cited

U.S. PATENT DOCUMENTS 4,351,949  9/1982  Larock ............................. 548/359
4,520,207  5/1985  Larock ............................. 549/60

*Primary Examiner*—Alan Siegel
*Attorney, Agent, or Firm*—Zarley, McKee, Thomte, Voorhees & Sease

[57] ABSTRACT

New organopalladium reactions involving the addition of thienylpalladium compounds to strained bicyclic alkenes, and subsequent chain extension reactions employing the chemistry of organopalladium compounds are disclosed. By these techniques a large number of bicyclic prostaglandin analogs are prepared, which are useful as inhibitors of arachidonic acid induced blood platelet aggregation, and are specific inhibitors of thromboxane synthetase.

6 Claims, No Drawings

SYNTHESIS OF THIOPHENE-CONTAINING PROSTAGLANDIN ENDOPEROXIDE APPARATUS

This is a division of application Ser. No. 423,789, filed Sept. 27, 1982, now U.S. Pat. No. 4,520,207.

BACKGROUND OF THE INVENTION

The mammalian hormones known as prostaglandins are an extremely important, biologically active class of C-20 unsaturated hydroxy acids first discovered in the 1930's. They have been found to have pronounced effects on the cardiovascular, respiratory and renal systems; the gastrointestinal tract; blood platelets and bone; the eye, skin, lungs and the reproductive organs. They appear to have pharmacological potential in the treatment of nasal congestion, stomach ulcers, hypertension, asthma, inflammation and thrombosis, as well as possible use in the induction of labor, termination of pregnancy, and utility in contraception. To date the major drawbacks to clinical application of the prostaglandins have been the very broad range of physiological activity prevalent in these compounds and their brief duration of action due to rapid metabolic deactivation. The desire for longer lasting drugs exhibiting much more specific activity has recently produced a number of very interesting analogs of prostaglandins and many structure-activity studies have resulted.

Tremendous potential also exists in the development of prostaglandin antagonists and reagents which will inhibit prostaglandin biosynthesis and metabolism. For this reason, there has been considerable work of late on the biosynthetic pathways involved in the formation of prostaglandins. This work has resulted in the recent discovery of intermediate prostaglandin endoperoxides and their biosynthetic products prostacyclin and the thromboxanes.

As biologically potent substrates, as well as key intermediates in prostaglandin biosynthesis, the endoperoxides have stimulated considerable recent synthetic effort. Some of these compounds are potent vasoconstrictors, stimulate smooth muscle contraction, induce the aggregation of human blood platelets, and inhibit $PGE_1$, $PGE_2$ and thromboxane biosynthesis.

With the recent discoveries of the highly active but very unstable prostacyclin and thromboxanes, attention has turned towards the synthesis of stable analogs of these compounds. Numerous prostacyclin analogs possessing substantial biological activity are now known. Similarly, the potent blood platelet aggregating and vasoconstrictor properties of thromboxane $A_2$ ($TXA_2$) have inspired other workers to synthesize each of the following stable analogs:

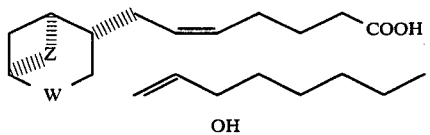

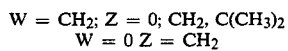

$W = CH_2; Z = O; CH_2, C(CH_3)_2$
$W = O\ Z = CH_2$

These compounds are inhibitors of $PGH_2$-induced aggregation of human blood platelets; have shown very potent vasoconstricting activity as well as behavior as a potent thromboxane $A_2$ antagonist on platelet aggregation, while selectively inhibiting the biosynthesis of thromboxanes; and selectively inhibit coronary artery constriction, platelet aggregation and thromboxane formation. The compound with $W=CH_2$, $Z=C(CH_3)_2$ has been suggested as a suitable antithrombotic agent.

From the above brief review, it should be quite obvious that the natural prostaglandins, the endoperoxides, prostacyclin and the thromboxanes display an extraordinary range of biological activity. The synthesis of stable analogs of these compounds shows tremendous promise of providing new compounds with more specific activity which will prove useful in the treatment of a vast array of human physiological ailments. Most syntheses to data have involved lengthy multi-step sequences or have begun with the natural prostaglandins. See for example, U.S. Pat. Nos. 4,065,472, and 4,258,053, for complex multi-step synthesis of thienyl-prostaglandin derivatives.

The primary objective of the present work is directed towards the development of entirely new synthetic routes to compounds of the type previously mentioned-routes which greatly shorten the present procedures, as well as provide a large number of new compounds, particularly bicyclic prostaglandin analogs prepared by the addition of thienyl-palladium compounds to strained bicyclic alkenes.

A further object is to prepare certain compounds of the type previously described which show substantial inhibition of arachidonic acid induced blood platelet aggregation and which appear to be very specific inhibitors of thromboxane synthetase.

The method, compounds and manner of performing the reactions and accomplishing the objectives of this invention are illustrated by the detailed description which follows hereinafter.

DETAILED DESCRIPTION OF THE INVENTION

The present invention relates to novel prostaglandin endoperoxide analogs, and to their production and use.

More particularly, this invention relates to novel bicyclic prostaglandin analogs, to pharmaceutical compositions containing at least one of the compounds, and to a process for the preparation of the compounds. The novel compounds of this invention are represented by the following formula:

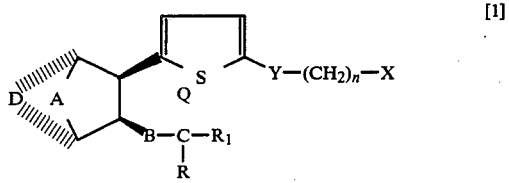

[1]

wherein n equals a whole integer of from 0 to 7, X is carboxylic acid, or $C_1$–$C_8$ ester, alcohol, ether, or amide groups, Y is ethylene or cis or trans vinylene; A is methylene, ethylene, oxy, imino, or lower alkyl, phenyl or aryl substituted imino; D is methylene, ethylene, vinylene, methyleneoxy, alkylidenedioxy, iminooxy, dithio, or azo; B is ethylene, cis and trans vinylene and ethynylene; R and $R_1$ are hydrogen, lower alkyl and lower aryl or $(CH_2)_Z$ with Z being 2 to 5, and Q is hydroxy, methoxy, acetoxy or hydrogen, or Q and R are both oxa.

In the significance as used above, it is possible for "n" to be from 0 to 12; however, since in the natural prostaglandins "n"=3, it has been found that the more one moves away from 3, the more unlikely that the compounds would have any specific activity. 0 to 7 are preferred with the most preferred being from 1 to 5, since this most nearly brackets, on both sides, the natural biologically active compounds.

The moiety represented by X is the easiest to change in the structure. It is not critical to the process or the products of this invention, and can be changed by conventional, routine chemistry. Most preferred is a carboxylic acid group since once again the natural prostaglandins have a carboxylic acid group at the X position. With other functional groups such as esters, alcohols, ethers and amides, preferably $C_1$ to $C_8$ groups are employed, and most preferably $C_1$ to $C_5$. "A" is preferably methylene or ethylene, but can also be oxygen, imino, or lower alkyl, phenyl, or aryl substituted imino groups. The term "lower" refers to having from $C_1$ to $C_8$.

"B" can be ethylene, cis and trans vinylene, and ethynylene. Since the natural prostaglandin compounds are the trans vinylene compounds, it may be more desirable to prepare the trans compounds; however, the cis compounds and ethynylene compounds also have substantial biological activity and can be prepared equally as satisfactorily.

"D" can be methylene, ethylene, vinylene, methyleneoxy, alkylidenedioxy, iminooxy, dithio or azo. D is preferably ethylene or vinylene.

"R" and "$R_1$" are hydrogen, lower alkyl and lower aryl, or $(CH_2)_z$, with Z being 2 to 5. The term "lower" is used in the same sense as previously defined.

Finally "Q" is selected from the group consisting of hydroxy, methoxy, acetoxy or hydrogen, or Q and R are both oxa. The compounds [I] have been found to possess the property of exhibiting substantial inhibition of arachidonic acid induced platelet aggregation.

The method of synthesis of these prostaglandin analogs can be generally summarized as an addition reaction of a thienylpalladium compound to bicyclic alkenes. More particularly, a thiophene is converted to a thienylmercurial, see Houben-Weyl, Vol. 13/2b, Georg Thieme Verlag, Stuttgart, pages 48-54, which is incorporated herein by reference. The thienylmercurial is reacted with dilithium palladium tetrachloride ($Li_2PdCl_4$) to give a thienylpalladium compound which is added to a bicyclic olefin to provide an addition compound, from which the palladium moiety is displaced by an acetylene or vinyl moiety, to provide the basic skeletal structure of [I]. Finally, protecting groups, if any, can be removed from the acetylene moiety to provide the desired endoperoxide prostaglandin analogs. The reaction is straightforward. It involves only two significant steps. Moreover, it achieves significant yields in comparison with complex procedures of the prior art. In particular, yields as high as 80% in each of the reactions steps can be obtained, with the resulting overall yield based on the amount of starting thiophene being as high as 30-40%. This is considered quite high in prostaglandin synthesis techniques.

In accordance with the first step, a thiophene starting material such as trans-3-(2)-thienylacrylic acid which is readily commercially available, is esterified by standard procedures to the corresponding methyl ester. Alternatively, the acid can be hydrogenated and acid-catalyzed esterification of it results in the corresponding saturated methyl ester. This is mercurated (for example with two equivalents of mercury chloride, in ten equivalents of sodium acetate with aqueous ethanol at the 5 position) to afford the corresponding organomercurial, that is, the thienylmercurial. These reactions are well known and may be summarized in the following scheme:

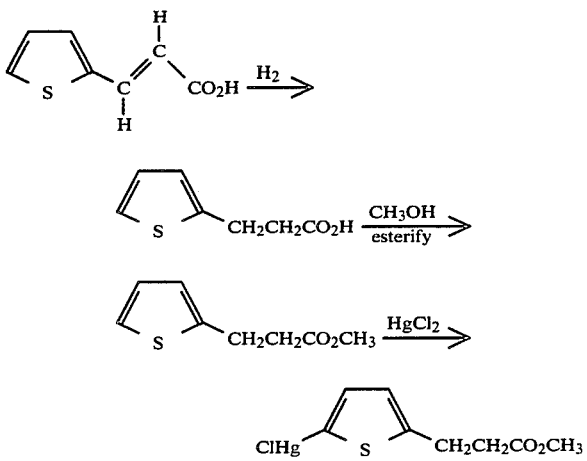

The hydrogenation step can also be omitted to obtain unsaturated thienylmercurials and the corresponding prostaglandins. Addition of these organomercurials to an acetonitrile solution of norbornene, palladium chloride and lithium chloride (10:1:>2) under nitrogen at 0° C. and warming to room temperature will afford thiophene-containing bicyclic organopalladium compounds in accordance with the following scheme:

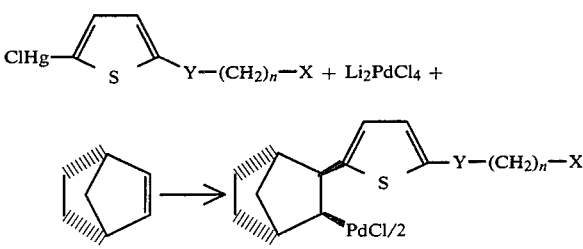

It thus can be seen that in the second step, and the first major part of this synthesis, the organomercurial is reacted with dilithium palladium tetrachloride and a bicyclic olefin to provide a bicyclic alkylpalladium compound which is represented by the immediately preceding formula.

The reaction is a simple addition reaction allowing for addition of the thienylpalladium compound to the bicyclic olefin.

In this reaction, as earlier stated and as depicted, the thienylpalladium compound is added to the bicyclic olefin, norbornene. Norbornadiene may also be used to form compounds of a nortricyclic structure as discussed later. Equally satisfactory synthesis results are achieved along with the essentially identical synthesis and chemistry. The starting structure is:

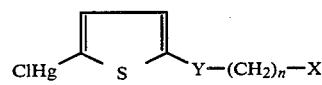

with X, Y and n as previously defined.

The next step and final major portion of the process involves applicant's most important contribution to the synthesis route of these thienylprostaglandins. That step is the discovery that the palladium moiety of the addition product of a thienylpalladium compound and a bicyclic olefin can be effectively displaced with an acetylene moiety by reacting with any protected lithium acetylide, as depicted below, preferably in the presence of, for example, two equivalents of triphenylphosphine to provide the skeletal structure of the endoperoxide prostaglandin analogs [Formula I]. It is represented by the following equation:

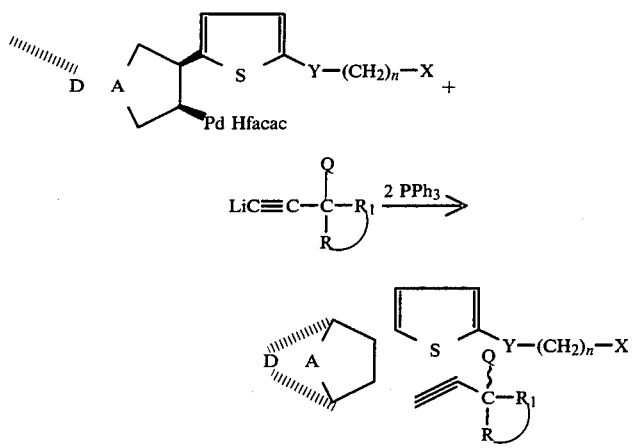

If it is desired that one have only double bond unsaturation in Formula I, the lithium acetylide carbon to carbon triple bond can be reduced to a cis double bond in near quantitative yield by simple hydrogenation. To prepare the trans double bond structure, a lithium divinyl cuprate, or a trialkylvinylstannane, in triphenylphosphine can be used to replace the lithium acetylide. For an alternative to the use of lithium divinyl cuprate, see Tetrahedron Letters, page 715 published 1982, which is incorporated herein by reference. This procedure may equally be used as opposed to the lithium divinyl cuprate, and in some instances, is preferred because it will provide better yields. Trans double bonds can also be introduced by treating the bicyclic organopalladium compound with carbon monoxide and triphenylphosphine followed by a trialkyl tin hydride to provide the corresponding aldehyde which can be converted to the trans allylic alcohol by Wittig olefination to an enone and subsequent metal hydride reduction.

The lithium acetylide preparation is the first thing to accomplish. The procedure is a known procedure for making lithium acetylides and is discussed in *The Chemistry of the Carbon-Carbon Triple Bond*, ed. S. Patai, J. Wiley and Sons, 1978, New York, which is incorporated herein by reference. For example, 1-octyn-3-ol-tetrahydropyranyl ether (OTHP) in tetrahydrofuran is deprotonated with normal butyl lithium to provide a representative lithium acetylide compound of the following formula:

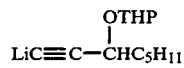

The acetylide displacement reaction is preferably begun at −78° C. and allowed to warm to room temperature. Typically, the temperature for this reaction may be from −20° C. to −78° C. The reaction times do not appear to be important, it merely being necessary that the ingredients are thoroughly mixed at low temperature. The reaction is preferably conducted in the presence of stirring. The reaction is conducted at low temperatures preferably, but it is all right to allow it to slowly warm to ambient conditions.

Pressure is not critical. The reaction is conducted in the presence of a solvent in order to allow intimate admixture of the reacting lithium acetylide and bicyclic olefin palladium addition compound. The precise solvent employed is not critical, but satisfactory results can be obtained with diethyl ether, and other standard aprotic solvents such as tetrahydrofuran and the like.

In the Formula last presented, the "OTHP" group is a representative protecting group of the "Q" moiety of the lithium acetylide.

The reaction is a simple displacement reaction and forms the basic skeleton of the desired thiophene-containing endoperoxide analog. The amount that is obtained is in typical instances about 60–70% of the starting organo-palladium compound, a high yield for a complex prostaglandin synthesis technique.

As a final step, the blocking or protecting group, that is, "Q", is removed by conventional techniques. Specifically for the OTHP group an ether cleavage can be accomplished by use of para-toluenesulfonic acid in methyl alcohol. It is preferred that "Q" be OTHP, although it it not essential. Another protecting group is an ester which can be removed by conventional ester hydrolysis to provide the corresponding alcohol group. This can be accomplished in the presence of a strong base, such as potassium hydroxide in methyl alcohol. These techniques will be further demonstrated in the specific examples.

The following examples are offered to further illustrate but not limit the process and compounds of the present invention.

EXAMPLES

Synthesis of the Organomercurials

Methyl trans-3-(2-thienyl)acrylate was prepared from the commercially available acid, by acid catalyzed esterification, in 88% yield. Methyl 3-(2-thienyl)propanoate was prepared by hydrogenation of the unsaturated acid followed by esterification in 79% overall yield.

These heterocycles were then mercurated using a modification of Volhard's procedure which is incorporated herein by reference, using two equivalents of $HgCl_2$ and ten equivalents of NaOAc in aqueous ethanol. The yields of the mercurials are given in Table I.

TABLE 1

| Synthesis of Mercurials | | |
|---|---|---|
| Heterocycle | Mercurial | % Yield |
| [thiophene-CO₂CH₃ structure] | [ClHg-thiophene-CO₂CH₃ structure] | 83 |

TABLE 1-continued

Synthesis of Mercurials

| Heterocycle | Mercurial | % Yield |
|---|---|---|
| [structure: thiophene-CH=CH-CO₂CH₃] | [structure: ClHg-thiophene-CH=CH-CO₂CH₃] | 86 |

Additions to bicyclic olefins

The next step involves transmetalation of the mercurials with palladium salts and addition to bicyclic olefins. The addition of methyl 3-(5-chloromercuri-2-thienyl)acrylate to norbornene was studied first. An initial attempt using THF as the solvent and an extractive work-up with ether afforded a low yield of product that was difficult to purify. However, addition of the mercurial to 0° C. solution of Li₂PdCl₄ and norbornene in acetonitrile and warming to room temperature gave the σ-palladium adduct in 67% yield after methylene chloride work-up. Addition of methyl 3-(5-chloromercuri-2-thienyl)propanoate to norbornene following the same procedure afforded the σ-palladium adduct in 78% yield.

The analogous reaction of methyl 3-(5-chloromercuri-2-thienyl)propanoate with norbornadiene-palladium dichloride gave the nortricyclo σ-palladium adduct in 74% yield.

Table II below shows the addition reaction to the bicyclic olefins and the thienylpalladium adduct as well as the yield obtained.

chloroform followed by 1.5–2.0 equivalents of hexafluoroacetylacetone.

The palladium chloride moiety, or the palladium acetate moiety, may be substituted by the techniques described earlier to obtain the appropriate prostaglandin type side chain. In particular, the unsaturated alcohol side chain of the prostaglandins was most easily introduced by a three step procedure involving (1) conversion of the organopalladium chloride to the corresponding hexafluoroacetylacetonate (Hfacac)(AgOAc followed by the diketone); (2) addition of 2 equivalents of triphenylphosphine in tetrahydrofuran (THF), cooling to −78° C., addition of a −78° C. THF solution of 1 equivalent of 1-lithio-3(2-tetrahydropyranyloxy)-1-octyne followed by slow warming to room temperature overnight and work-up; and (3) removal of the THP protecting group (cat. p-TsOH in methanol, 4–6 hours at room temperature). This approach affords exclusively the exo isomers. In this manner the novel thiophene-containing prostaglandin endoperoxide analogs: X is $CO_2CH_3$, Y is CH=CH, n=0, A is $CH_2$, D is $CH_2CH_2$, B is C≡C, Q is OH, R is H, $R_1$ is $C_5H_{11}$ is obtained (64% overall yield). The corresponding com-

TABLE 2

Addition to Bicyclic Olefins

| Organomercurial | Olefin | σ-Palladium adduct | % Yield |
|---|---|---|---|
| [ClHg-thiophene-CH=CH-CO₂CH₃] | [norbornene] | [adduct structure with PdCl/2] | 78 |
| [ClHg-thiophene-CH₂CH₂-CO₂CH₃] | " | [adduct structure with PdCl/2] | 67 |
| [ClHg-thiophene-CH₂CH₂-CO₂CH₃] | [norbornadiene] | [nortricyclo adduct structure with PdCl/2] | 74 |

Reactions with 1-lithio-3-(2-tetrahydropyranyloxy)-1-octyne

Previous work has shown that reactions of bicyclic organopalladium compounds with lithium acetylides proceed more cleanly and in higher yield when the chloride anion on palladium is exchanged for hexafluoroacetylacetonate. This was accomplished by treating the palladium complex with 1 equivalent of AgOAc in pounds where X=$CO_2H$, Y=CH=CH, n=0 (96% yield); X=$CO_2CH_3$, Y=$CH_2CH_2$, n=0, (58% yield) and X=$CO_2H$, Y=$CH_2CH_2$, n=0 (82% yield) were also obtained with A, B, D, Q, R and R' as just above defined. The acids are obtained by saponification of the corresponding esters.

Via a similar lithium acetylide substitution reaction, the σ-palladium adduct last listed in Table II was carried on to:

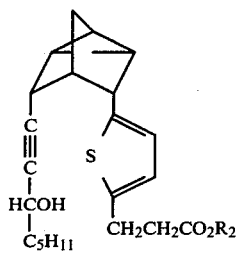

wherein $R_2$ was $CH_3$. Saponification converted the methyl group to hydrogen.

The σ Palladium adduct first listed in Table II has also been reacted with a lithium divinyl cuprate, as discussed previously, to give a prostaglandin analog with $X=CO_2CH_3$, $Y=CH_2CH_2$, $n=0$, $A=CH_2$, $D=CH_2CH_2$, $B=$ trans $CH=CH$, $Q=OH$, $R=H$, $R_1=C_5H_{11}$.

Incorporation of the thiophene ring into prostaglandin endoperoxide analogs has several very attractive features. First of all, a number of heterocyclic prostaglandin analogs have already shown substantial biological activity. Introduction of a phenyl unit in the acid side chain has also provided a number of compounds of biological interest. The heterocyclic ring also forces the acid side chain to adopt a configuration analogous to the cis-5,6 olefinic side chain found in the naturally occurring prostaglandins. Finally, the thiophene ring provides a site for further chemical elaboration.

What is claimed is:

1. Thiophene-containing prostaglandin endoperoxide analogs of the formula:

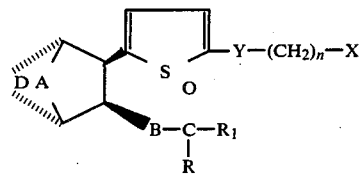

wherein n equals a whole integer of from 0 to 7, X is carboxylic acid, or $C_1$-$C_8$ ester, alcohol, ether or amide groups; Y is ethylene or cis or trans vinylene; A is methylene, ethylene, oxy, imino, or lower alkyl, phenyl or aryl substituted imino; D is methylene, ethylene, vinylene, methyleneoxy, alkylidenedioxy, iminooxy, dithio, or azo; B is ethylene, cis and trans vinylene, and ethynylene; R and $R_1$ are hydrogen, lower alkyl and lower aryl or $(CH_2)_Z$ with Z being 2 to 5, and Q is hydroxy, methoxy, acetoxy or hydrogen, or Q and $R_1$ are oxa.

2. The compounds of claim 1 wherein n is from 1 to 5.

3. The compounds of claim 2 wherein X is a carboxylic acid group.

4. The compounds of claim 1 wherein A is selected from the group of methylene or ethylene.

5. The compounds of claim 3 wherein B is selected from the group consisting of ethylene, and cis and trans vinylene.

6. A prostaglandin analog comprising:

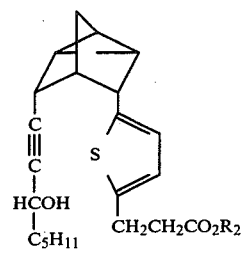

wherein $R_2$ is selected from the group consisting of hydrogen and methyl.

* * * * *

UNITED STATES PATENT AND TRADEMARK OFFICE
CERTIFICATE OF CORRECTION

PATENT NO. : 4,563,537
DATED : January 7, 1986
INVENTOR(S) : Richard C. Larock

It is certified that error appears in the above-identified patent and that said Letters Patent is hereby corrected as shown below:

In the Title:

SYNTHESIS OF THIOPHENE-CONTAINING PROSTAGLANDIN ENDOPEROXIDE ANALOGS

Signed and Sealed this

First Day of April 1986

[SEAL]

Attest:

Attesting Officer

DONALD J. QUIGG

Commissioner of Patents and Trademarks